US008617133B2

(12) United States Patent
Muramatsu et al.

(10) Patent No.: US 8,617,133 B2
(45) Date of Patent: Dec. 31, 2013

(54) MULTI-CHAMBER CONTAINER

(75) Inventors: Yasuhiro Muramatsu, Shizuoka (JP); Kaoru Shimizu, Shizuoka (JP)

(73) Assignee: Ajinomoto Co., Inc., Tokyo (JP)

(*) Notice: Subject to any disclaimer, the term of this patent is extended or adjusted under 35 U.S.C. 154(b) by 535 days.

(21) Appl. No.: 12/688,427

(22) Filed: Jan. 15, 2010

(65) Prior Publication Data

US 2010/0179505 A1 Jul. 15, 2010

Related U.S. Application Data

(63) Continuation of application No. PCT/JP2008/060334, filed on Jun. 5, 2008.

(30) Foreign Application Priority Data

Jul. 17, 2007 (JP) ................................ 2007-186024

(51) Int. Cl.
*A61B 19/00* (2006.01)

(52) U.S. Cl.
USPC .............................. 604/410; 53/440; 156/290

(58) Field of Classification Search
USPC ............ 604/410, 335, 17, 19, 403, 408, 917; 426/128; 156/290; 53/440
See application file for complete search history.

(56) References Cited

U.S. PATENT DOCUMENTS

| | | | | |
|---|---|---|---|---|
| 2007/0060903 | A1 | 3/2007 | Miyajima et al. | |
| 2008/0033390 | A1* | 2/2008 | Kitagawa et al. | 604/408 |
| 2009/0254032 | A1 | 10/2009 | Muramatsu | |
| 2010/0010466 | A1 | 1/2010 | Muramatsu | |

FOREIGN PATENT DOCUMENTS

| | | |
|---|---|---|
| JP | 08-052196 | 2/1996 |
| JP | 2003-159309 | 6/2003 |
| JP | 2004-248892 | 9/2004 |
| JP | 2006-507914 | 3/2006 |
| JP | 2006-087904 | 4/2006 |
| JP | 2006-255406 | 9/2006 |
| WO | WO 2006/006513 | 1/2006 |
| WO | WO 2007/055355 | 5/2007 |
| WO | WO 2008/136452 | 11/2008 |

OTHER PUBLICATIONS

U.S. Appl. No. 12/606,384, filed Oct. 27, 2009, Shimizu, et al.
U.S. Appl. No. 12/706,381, filed Feb. 16, 2010, Muramatsu, et al.
Japanese Office Action issued Jul. 12, 2012, in Japan Patent Application No. 2009-523571 (with English translation).
Office Action issued Mar. 26, 2013 in Japanese Application No. 2009-523571 (with English translation).

* cited by examiner

*Primary Examiner* — Jacqueline Stephens
*Assistant Examiner* — Benedict L Hanrahan
(74) *Attorney, Agent, or Firm* — Oblon, Spivak, McClelland, Maier & Neustadt, L.L.P.

(57) ABSTRACT

A multi-chamber container includes a medical bag made of a flexible film for storing medicines, and an outlet port mounted to the bag for discharging medicines. The bag has partition wall dividing the bag into compartments for medicines, the wall has welded portion separated by pressing to the bag, the port has extended portion extending to inside the bag and closure member integral with the port and having U-shaped profile, the member has sealed point connected to the bag such that the member is opened by expansion of the bag when the wall separates, the extended portion has recess and thin wall portion connecting to the member, the thin wall portion is broken by the expansion of the bag such that the member is pulled by the sealed point, hinges at the recess and is opened, and the sealed point is positioned away from the recess and toward the wall.

15 Claims, 12 Drawing Sheets

MULTI-CHAMBER CONTAINER

TECHNICAL FIELD

The present invention relates to a multi-chamber container having an outlet port, which is usually in a closed condition and which is opened in cooperation with a deformation of a medical deformation of a medical bag as generated when the latter is opened.

BACKGROUND TECHNOLOGY

A multi-chamber container for an infusion is known, which is provided with a medical bag formed with a flexible or soft film and having opposed faces, which are welded at a relatively low temperature to form a weak seal (partition wall) for creating a plurality of compartments or cells for respective storage of different medical liquids. At the outer periphery of the medial bag, an outlet port as a plastic molded product is provided, which outlet port forms a tubular shape having an inner space provided with a first end opened to one of the compartments and a second end fitted with a rubber plug. Prior to giving the medical liquids to a patient, the medical bag is subjected to a pressing from its outside, so that the weak seal is separated and opened, causing the space inside the bag to be unified, resulting in a mixing of the medical liquids. Thus, a piecing of the rubber plug by a needle of an infusion unit allows the medical liquids to be given. In short, in this mixing type of container for medical use, an operation for opening the weak seal for obtaining the mixing of medical liquids is essential prior to the commencement of an administration. By a piercing of the rubber plug without opening the weak seal, an erroneous operation is likely that an administration of medical liquid only at the compartment adjacent the outlet port is done. In order to combat this problem, an improved construction of an outlet port has been proposed, wherein the outlet port has a breakable end wall in the medical bag, from which breakable end wall stress imparting parts are integrally extended in a manner that the stress imparting parts are firmly welded to the respective opposed inner surfaces of the medical bag. The stress imparting parts are opened in cooperation with an inflated deformation of the medical bag as obtained when opening the compartments in a manner that a breakage of the end wall of the outlet port occurs, which causes the outlet port to be connected with the space inside the medical bag. See patent publication No. 1.

Patent Publication No. 1: Japanese Un-examined Patent Publication No. 2006-87904

DISCLOSURE OF THE INVENTION

Problem to be Solved by the Invention

In Patent publication No. 1, the opening of outlet port is obtained by breakage of the end wall (breakable part) of the outlet port by a stress as applied from the stress imparting part integrally extending from the end wall and cooperating with the expanded deformation of the medical bag as obtained when the partition wall is opened. In this patent publication, the stress imparting parts extend from the breakable part at the tip end of the outlet port while being spaced from the tip end. Such an arrangement is intended for connection of the stress imparting parts to the medical bag at a location of an increased expanded deformation as obtained when the bag being opened, thereby obtaining an increased expansion of the stress imparting parts, i.e., a positive breakage and opening of the breakable part integrally connected to the root portions of the stress imparting parts. However, it is likely that a positive breakage of the breakable part at the opening can not be obtained due to the small deformation amount as obtained by the breakable part located, itself, at the end of the outlet part.

Furthermore, the breakable part in the prior art closes normally the outlet port completely. In this completely closed structure, a vapor in the medical bag cannot be used for executing sterilization under wet heat condition. Therefore, in order to execute sterilization under wet heat condition, an additional process is needed for introducing an amount of liquid such as water into the outlet port or another principle of sterilization process such as those using a radiation is needed, which makes the process to be complicated, on one hand and, on the other hand, the cost to be increased.

In view of the above difficulties, the present invention aims to obtain a positive opening f the outlet port upon the separation of partition wall. In addition, the present invention aims to obtain a positive sterilization under wet heat condition using vapor of the medicines stored in the medical bag.

Means for Solving Problems

According to the first invention, a multi-chamber container is provided, which comprises: a medical bag made of flexible film; an outlet port mounted to the medical bag for discharging medicines; a partition wall for dividing the inside of the medical bag into compartments for storage of respective medicines therein, said partition wall being formed by welding opposed inner surfaces of the medical bag in a manner that the welded portion is separated by a pressing force applied to the medial bag from its outside for causing the medicines stored in the respective compartments to be mixed with each other, said outlet port having a portion extending inwardly to the medial bag, and; a closure member mounted to said inwardly extended portion of the outlet port and closing substantially the outlet port to the inside of the medical bag at the normal condition, said closure member being connected to the opposed surface of the medical bag, said closure member being opened by an outside force which is generated in cooperation with the expansion of the medical bag as obtained when the partition wall is separated and opened in a manner that a portion of the outlet port as occupied by the closure member during non-opened condition becomes, per se, an opening for causing the outlet port to communicate with the inside of the medical bag.

According to the second invention, a multi-chamber container is provided, which comprises: a medical bag made of flexible film; an outlet port mounted to the medical bag for discharging medicines; a partition wall for dividing the inside of the medical bag into compartments for storage of respective medicines therein, said partition wall being formed by welding opposed inner surfaces of the medical bag in a manner that the welded portion is separated by a pressing force applied to the medial bag from its outside for causing the medicines stored in the respective compartments to be mixed with each other, said outlet port having a portion extending inwardly to the medial bag, and; a closure member mounted to said inwardly extended portion of the outlet port and closing substantially the outlet port to the inside of the medical bag at the normal condition, said closure member being connected to the opposed surface of the medical bag in a manner that the closure member is opened by an outside force generated in cooperation with the expansion of the medical bag as obtained when the partition wall is separated in order to form an opening for communicating the outlet port with the inside of the medical bag, the opening of the outlet port being done substantially only at one of the sides of the outlet port.

According to the third invention, a multi-chamber container is provided, which comprises: a medical bag made of flexible film; an outlet port mounted to the medical bag for discharging medicines; a partition wall for dividing the inside of the medical bag into compartments for storage of respective medicines therein, said partition wall being formed by welding opposed inner surfaces of the medical bag in a manner that the welded portion is separated by a pressing force applied to the medial bag from its outside for causing the medicines stored in the respective compartments to be mixed with each other, said outlet port having a portion extending inwardly to the medial bag, and; a closure member mounted to said inwardly extended portion of the outlet port and closing substantially the outlet port to the inside of the medical bag at the normal condition, said closure member being connected to the opposed surface of the medical bag in a manner that the closure member is opened by an outside force generated in cooperation with the expansion of the medical bag as obtained when the partition wall is separated in order to form an opening for communicating the outlet port with the inside of the medical bag, the extended portion of the outlet port for the provision of the closure member being in a offset relationship with respect to the axis of the outlet port.

According to the fourth invention, a multi-chamber container is provided, which comprises: a medical bag made of flexible film; an outlet port mounted to the medical bag for discharging medicines; a partition wall for dividing the inside of the medical bag into compartments for storage of respective medicines therein, said partition wall being formed by welding opposed inner surfaces of the medical bag in a manner that the welded portion is separated by a pressing force applied to the medial bag from its outside for causing the medicines stored in the respective compartments to be mixed with each other, and; a closure member mounted to a location of the outlet port located inside the medical bag, the closure member closing substantially the outlet port to the inside of the medical bag at the normal condition, said closure member being opened by an outside force generated in cooperation with the expansion of the medical bag as obtained when the partition wall is separated in order to form a first opening for communicating the outlet port with the inside of the medical bag, said outlet port forming a second opening, which connects the outlet port to the inside of the medical bag in order to sterilize the outlet port under a wet heat condition, the second opening being closed by the opposed surface of the medical bag during the normal condition.

According to the fifth invention, a method is provided for sterilization comprising the steps of:

providing a multi-chamber container comprising: a medical bag made of flexible film; an outlet port mounted to the medical bag for discharging medicines; a partition wall for dividing the inside of the medical bag into compartments for storage of respective medicines therein, said partition wall being formed by welding opposed inner surfaces of the medical bag in a manner that the welded portion is separated by a pressing force applied to the medial bag from its outside for causing the medicines stored in the respective compartments to be mixed with each other; an opening formed in the outlet port for communication of the outlet port to the inside of the medical bag when an infusion is done, and; a closure member connected to the opposed surface of the medical bag and closing substantially the outlet port during a normal condition;

forming a second opening in the outlet port;

heating the medicines in the medical bag while the second opening is opened in order to sterilize the outlet port under wet heat condition, and;

sealing the second opening by the opposed surface of the medical bag after completion of the sterilizing step.

According to the sixth invention, in a method for molding a multi-chamber container comprising: a medical bag made of flexible film; an outlet port mounted to the medical bag for discharging medicines; a partition wall for dividing the inside of the medical bag into compartments for storage of respective medicines therein, said partition wall being formed by welding opposed inner surfaces of the medical bag in a manner that the welded portion is separated by a pressing force applied to the medial bag from its outside for causing the medicines stored in the respective compartments to be mixed with each other, and; a closure member mounted to a location of the outlet port located inside the medical bag, the closure member closing substantially the outlet port to the inside of the medical bag at the normal condition, said closure member being opened by an outside force generated in cooperation with the expansion of the medical bag as obtained when the partition wall is separated in order to form a first opening for communicating the outlet port with the inside of the medical bag, said outlet port forming a second opening, which connects the outlet port to the inside of the medical bag in order to sterilize the outlet port under a wet heat condition, the second opening being closed by the opposed surface of the medical bag during the normal condition, an improvement is provided, which comprises the steps of:

providing a mold comprising an outer die set and an inner die set, between which a cavity corresponding a profile of said outlet port is created;

locating a portion of the mold for forming said closure member in a manner that to said portion, a portion of the mold for forming the second opening is opposed, and;

introducing welded plastic material into said cavity, thereby executing the molding process.

Effects of the Invention

In the first invention, the closure member, which seals the outlet port, is broken or rotated by an expanded deformation of the medical bag as generated by its opening in a manner that a portion of the outlet port as occupied by the closure member during non-opened condition becomes, per se, an opening for making the outlet port to communicate with the inside of the medical bag. As a result, an opening of the outlet port in cooperation with the opening of the medical bag is reliably obtained.

In the second invention, the opening of the outlet port is done at its single side. Therefore, a single provision of a closure member is enough for a desired operation, which makes the construction to be simplified.

According the third embodiment, an offset arrangement of the location of the closure member in the outlet port with respect to the axis of the outlet port makes it possible that an increased outside force applied to the closure member via the welded portion is obtained when opening the medical bag, resulting in a reliable opening operation. In this invention, it is preferable that the closure member is arranged only at the side of an increased offset amount and is desirable for obtaining a reliable opening operation. Furthermore, an arrangement may be possible that the welded portion opposite to the closure member is located adjacent the space inside the medical bag and is also preferable for obtaining an increased operational reliability.

According to the fourth and fifth inventions, the opened condition of the second hole allows a vapor of the medical liquid in the medical bag to be generated by a heating, which vapor is introduced into the outlet port by way of the second hole and is filled inside the outlet port, resulting in a sterilization of the outlet port under a wet heat condition, thereby obtaining an increased sterilizing performance.

In the first to fourth inventions, it is preferable that the closure member is rotatable and a weak or breakable part is provided for integrally connection of the closure member to the remaining part of the outlet port. By this arrangement, a molding process can be easily practiced, on one hand and, on the other hand, a reliable opening operation can be obtained.

The weak part integrally connects, normally, the closure member with the remaining part of the outlet port and is broken when opening the bag, resulting in an increased reliability of the opening operation. Furthermore, the outlet port is made as an injection molded product from a resin material and, in this case, it is preferable that a die set for molding is of an opened structure not only from the view point of an efficiency of a die releasing operation but also from the view point of an increased service life of the die set. After the execution of molding process, a secondary process such as welding is done for obtaining a sealing or closure of the opened portion of the product.

Furthermore, the outlet port may be provided with an inclined wall for mounting the closure member, which is also effective for obtaining a reliable opening operation.

According to sixth invention, a desired centered position of the core pin with respect to the die set is obtained regardless a flow resistance of the resin when a molding of an outlet port from a plastic material is done, thereby obtaining an outlet port as a molded product of a desired and uniformed wall thickness.

BRIEF EXPLANATION OF ATTACHED DRAWINGS

BRIEF EXPLANATION OF REFERENCE NUMERALS

10: Medical Bag
12: Outlet Port
12-1: Base Portion of Outlet Port
12-6: Rectangular Cross-Sectional Part of Outlet Port
14: Strong Seal
18: Weak Seal (partition wall of the present invention)
20, 22: First, Second Compartment
26: Inner Rubber Plug
30: Groove
30': Weak Portion
32: Integral Hinge
33: U-Shaped Portion
34: Point Seal
36: Aperture

BEST MODES FOR PRACTICING THE INVENTION

Figure 1:
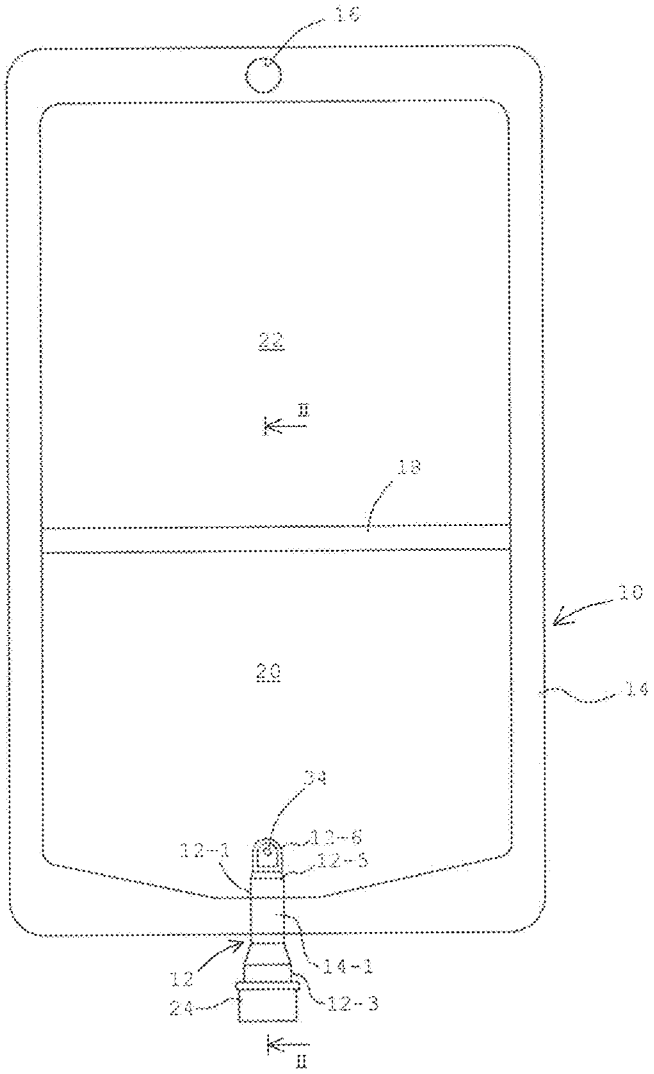
FIG. 1 is a plan view of a multi-cell container according to the present invention.
Figure 2:
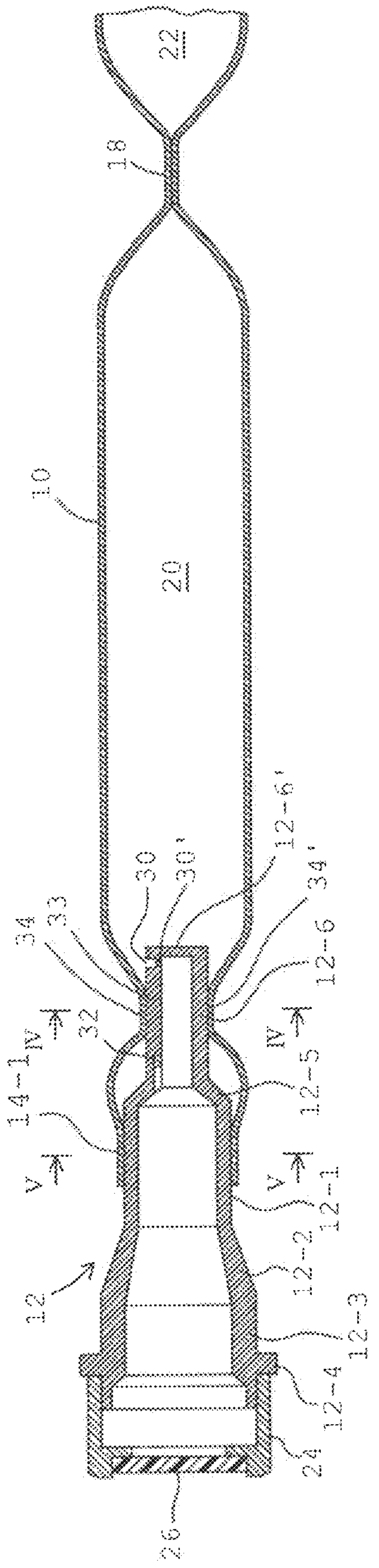
FIG. 2 is a partial enlarged cross-sectional view of the container according to the present invention, taken along lines II-II in FIG. 1.

In FIGS. 1 and 2, a container according to the present invention is shown, which includes a medical bag or outer bag 10 of a flat shape for a storage of medicines and an outlet port 12 connected to the medical bag at its outer peripheral portion. The medical bag 10 is constructed by a multi-layered film as a flexible material according to the present invention, such as a polyethylene film of a thickness for example of 200μ. A pair of the synthetic resin films is subjected to a pressing at their peripheral portions at a temperature fully higher than the softening temperature, which is about 130° C. in case of polyethylene, so that a strong seal 14 is created, thereby forming a bag of substantially rectangular shape. The medical bag 10 is not necessarily limited to the above type made from cuts of film. As an alternative, a container may be formed from a bag made of a tubular inflation film or made by blowing. The strong seal 14 forms a suspension hole 16, by using which the medical bag 10 is held and suspended to a dripping stand in order to practice an operation such as an infusion or dripping.

At a substantially middle location along the length, the medical bag 10 forms a weak seal 18 as a partition wall according the present invention, whereat the opposed top and bottom inner surfaces of the medical bag are welded, so that the inner cavity of the medical bag is divided into a first compartment or cell 20 and a second compartment or cell 22. The first compartment stores therein with first medicine(s) and the second compartment 22 stores therein with second medicine(s). The weak seal 18 is constructed by pressing the opposed top and bottom surfaces of cuts of the synthetic resin film constructing the medical bag 10 at a temperature of 120° C. in case of polyethylene, which is, to some extent, larger than its softening temperature. The first and second cells 20 and 22 are filled with respective medical liquids. At a location of the cell 20 or 22, an outside pressing of the medical liquid generates, therefore, a fluid pressure (liquid pressure as caused by pressing), which causes the weak seal 18 to be separated and opened while the strong seal 14 being maintained, resulting in a mixing of the first and second medical liquids.

Figure 3:
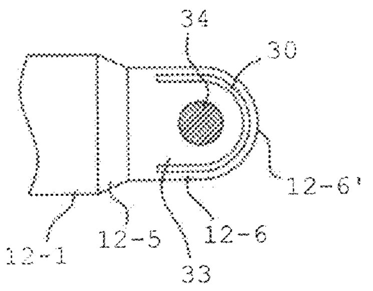
FIG. 3 is a partial enlarged view of a front portion of the outlet port in FIG. 1.
Figure 4:
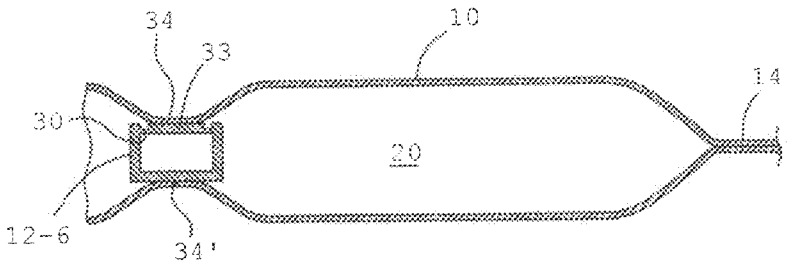
FIG. 4 is a cross-sectional view taken along lines IV-IV in FIG. 2.
Figure 5:
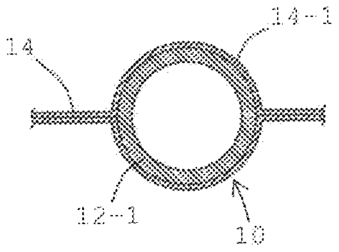
FIG. 5 is a cross-sectional view taken along lines V-V in FIG. 2.

The outlet port 12 is a mold product from a synthetic resin of an enough value of thickness, which allows the port to keep its shape and which is preferably made of the same plastic material as that of the medical bag 10 in order to obtain a desired adherence of the port 12 to the bag 10. The outlet port 12 forms generally a tubular shape and has a base portion 12-1 of a circular cross-sectional shape, to which base portion the top and bottom synthetic resin films are strongly welded. The welded portions of the films construct a part 14-1 of the strong seal 14 at the periphery of the outlet port 12. The outlet port 12 is, at the location outward from the base portion 12-1, formed with a tapered part 12-2, which is connected with a diameter expanded part 12-3. The expanded part 12-3 is, at its outer end, formed with a flange 12-4, to which a cap 24 is abutted and welded. The cap 24 is, at its bottom, formed with an opening, to which an inner plug 26 made of a rubber material is fitted. Upon an infusion process such as dripping, a piecing of the rubber plug 26 by a needle of not shown infusion set is done. As a result, the space inside the medical bag 10 is connected to an infusion tube, which allows an infusion process to be practiced. The base portion 12-1 extends into the space inside the medical bag 10 and is connected, via a tapered portion 12-5, to a end portion 12-6 of a rectangular cross-sectional shape as an extended part of the outlet port to the inside of the medical bag according to the present invention. The rectangular cross-sectional portion 12-6 has a rounded and closed end surface 12-6' as viewed from the above (FIG. 3). The rectangular cross-sectional portion 12-6 has an upper wall, which is formed with a groove 30 along the outer periphery. The groove 30 forms U-shape when viewed from the above and has ends extending to locations adjacent the portion for connection of the portion 12-6 to the taper portion 12-5. At the bottom of the groove 30, the wall thickness is reduced, so that a thin walled portion 30' as a weak part is created, which is broken by an outside force as generated when the medical bag is opened. A portion of U-shaped profile 33 is created inwardly of the groove 30, which functions as a closure member according the present invention. In other words, in this embodiment of the present invention, the portion 33 of U-shaped profile as a closure member is integrated with the remained portion of the outlet port 12 via the groove 30 or thin walled portion 30', which portion 33 normally closes or separates the outlet port 12 from the medical bag 10. Furthermore, the rectangular cross-sectional portion 12-6 is, at the inner surface of its upper wall, formed with a recess 32, which extends along the width. When the upper wall of the rectangular cross-sectional portion 12-6 is broken and separated at the groove 30 by the outside force as generated by the opening of the weak seal 18, the recess 32 functions as a base point, i.e., an integrated hinge structure for obtaining a pull tab mannered rotating movement of the portion 33 of U-shaped profile located inside the broken and separated part. In short, among the top and bottom sides of the medical bag faced with the outlet port 12, the portion 33 of U-shaped profile is located only at the upper side. In other words, according to the present invention, the portion 33 functions as a closure member of the outlet port 12 only at s side thereof.

A welding at a point like area (so-called point welding) of the portion 33 of U-shaped profile to the inner surface of the synthetic resin film constructing the medical bag is done by using welding means such as laser welder. The reference numeral 34 schematically illustrates the resultant welded area by the point welding. A welding temperature at the point sealed area 34 corresponds to that for obtaining the strong seal 14. Therefore, at the area, a non-separable connection of the portion 33 of U-shaped profile to the film is obtained. As a result, as will be explained later, the U-shaped profile portion 33 is subjected to a stretching force in cooperation with an expansion of the medical bag at the connected portion to the outlet port as obtained upon the opening of the weak seal 18, so that the U-shaped profile portion 33 is broken and opened at the weak part 30'. In order to effectively transmit the outside force to the sealed point 34 by the expanded deformation of the medical bag as generated upon the opening of the bag, it is needed that the outlet port 12 is welded to the faced surface of the medical bag also at the side opposite the point seal 34, i.e., at the bottom wall of the rectangular cross-sectional portion 12-6 opposite to the top wall on which the U-shaped profile portion 33 is formed. A reference numeral 34' denotes such a weld at the bottom wall.

Figure 6:
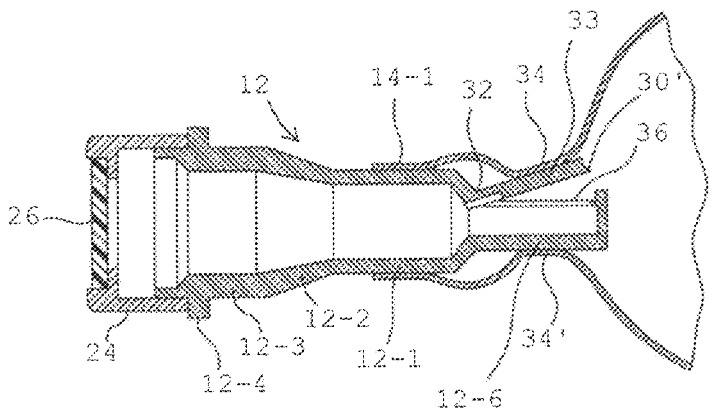
FIG. 6 is a partial view of a connection part of the outlet port to the medical bag when being opened.

When commencing opening operation, the medical bag is rested on a suitable object such as desk et al, and is subjected to a pressing by a palm et al at the location of the bag where the medical liquid stored. As a result of the pressing, a hydraulic pressure is applied to the weak seal 18, so that the top and bottom synthetic resin film layers constructing the weak seal 18 are separated and opened. At the instant of the opening of the weak seal 18, the medical bag 10 is subjected to an expansion. Due to the fact that the U-shaped profile portion 33 is firmly integrated to the opposed inner surface of the medical bag by the point seals 34 and 34', the expansion of the medical bag causes an outside force to be generated in the U-shaped profile portion 33 in the direction for expanding the bag, so that the U-shaped profile portion 33 is rotated outwardly about the integrated hinge 32 as shown in FIG. 6. As a result, an aperture 36 as an opening or first opening of the present invention is created for communication of the inside of the medical bag to the inside of the outlet port 12, which allows the medicines inn the medical bag to be introduced into the outlet port 12.

In the above embodiment, a portion of the outlet port 12 as occupied by the U-shaped profile portion 33 as the closure member during non-opened condition becomes, per se, the opening 36 for a communication of the inside of the medical bag 10 to the outlet port 12. Since the degree of the opening of the U-shaped profile portion 33 as the closure member upon the separation of the medical bag 10 becomes, per se, the degree of the opening for connecting the inside of the medical bag to the outlet port, a reliable opening of the outlet port 12 as well as a desired degree of opening, i.e., a flow amount can be obtained.

Figure 7A:
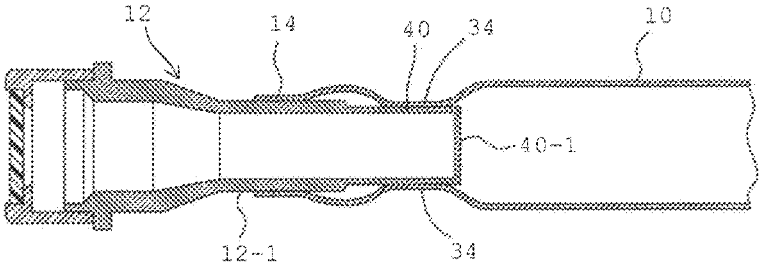
FIG. 7 is a partial view of a connection part of the outlet port to the medical bag when being opened in another embodiment, (*a*) showing an opened condition, (*b*) showing an opened condition.
Figure 7B:
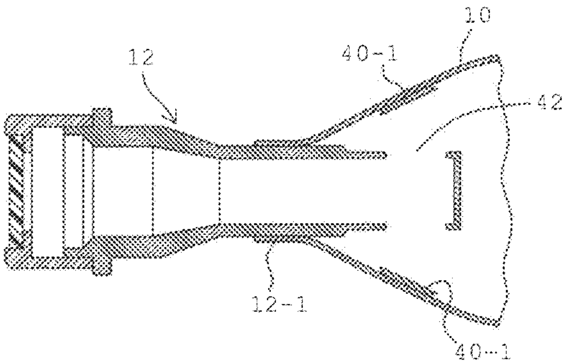

FIG. 7 illustrates another embodiment, where the outlet port 12 has a tubular part 40, which extends into the inside of the medical bag from the base portion 12-1. The tubular part 40 has a closed end 40-1 and is entirely thin walled. The top and bottom synthetic resin film layers constructing the medical bag 10 is strongly, i.e., non-separably connected to the opposed surfaces of the thin walled tubular part 40 at the seals 34. The tubular part 40 functions as a closure member of the present invention.

By an expansion of the medical bag as shown by FIG. 7(*b*) when the medical bag is opened, an outside force is applied to the thin wall portion 40 of the outlet port welded to the medical bag, by which outside force the thin wall portion 40 is broken, so that the space inside the medical bag is in communication with space inside the outlet port 12. FIG. 7(*b*) illustrates that the welded portion 40-1 to the medical bag of the thin walled tubular part 40 is separated and an opening 42 is formed for communicating the inside of the medical bag to the inside of the outlet port. It should be noted that the manner of the breakage of the thin walled tubular part 40 is not necessarily limited to the version as illustrated in FIG. 7(*b*). As an alternative, a construction may be possible that the part 40 is entirely broken to pierces or the part 40 is broken only at a single side.

Figure 8A:
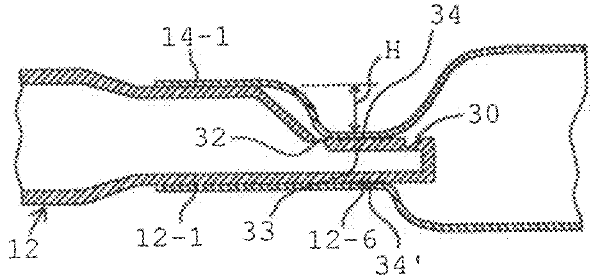
FIG. 8 is a partial view of a connection part of the outlet port to the medical bag when being opened in further another embodiment, (*a*) showing an opened condition, (*b*) showing an opened condition.
Figure 8B:
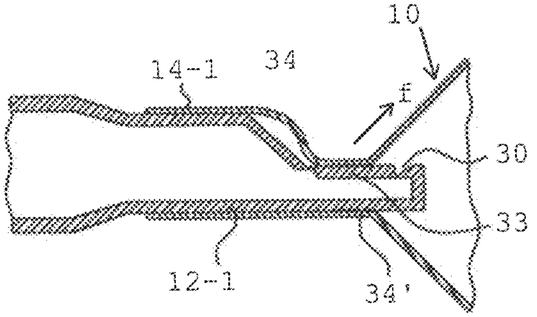

FIGS. 8(*a*) and 8(*b*) illustrate further another embodiment. In a non-opened condition as shown in FIG. 8(*a*), the rectangular cross-sectional portion 12-6 of the outlet port 12 extended into the inner cavity of the medical bag is under a offset arrangement with respect to the axis of the outlet port 12. In the embodiment, the rectangular cross-sectional portion 12-6 has a bottom wall, which is flashed with the base portion 12-1 of the outlet port. However, at the top wall, the portion 12-6 is lowered from the base portion and H illustrates a difference in the height. The U-shaped profile portion 33 as the closure member is formed on the top wall of the rectangular cross-sectional portion 12-6. As similar to the first embodiment in FIG. 3, the portion 12-6 is integrally formed with the remained part of the outlet port via the U-shaped groove 30 as a weak or breakable part. In FIG. 8, the synthetic resin film constructing the medical bag 10 is, at its top layer, point sealed (34) to the U-shaped profile portion 33 and is, at its bottom layer, point sealed (34') to the bottom wall of the rectangular cross-sectional portion 12-6, as similar to the embodiments as already explained. In FIG. 8 as well as the following FIG. 9, the point seals 34 and 34' are illustrated by lines of an increased thickness than those of remaining parts for discrimination purpose.

FIG. 8(*b*) illustrates an expanded condition of the medical bag as separated. A force f is applied to the portion 33 of U-shaped profile, so that a breakage of the portion 33 occurs at the groove 30 as a weak part, resulting in a rotating movement of the U-shaped profile portion 33, resulting in an opened condition of the outlet port 12. This operation is similar to those explained with reference to the preceding embodiments. In addition, due to an increased degree H of the offset amount of the U-shaped profile portion 33 as the closure member welded to the top layer of the synthetic resin film constructing the medical bag 10 with respect to the welded portion 14-1 (strong seal) of the medical bag to the outlet port 12, an increased force f as applied to the U-shaped profile portion 33 as generated by the expanded displacement of the medical bag 10 is obtained.

Figure 9A:
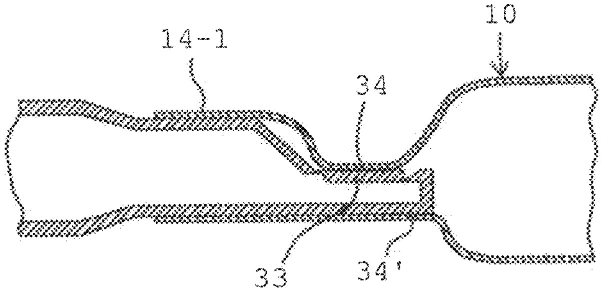
FIG. 9 is a partial view of a connection part of the outlet port to the medical bag when being opened in a modification of that in FIG. 8, (*a*) showing an opened condition, (*b*) showing an opened condition.
Figure 9B:
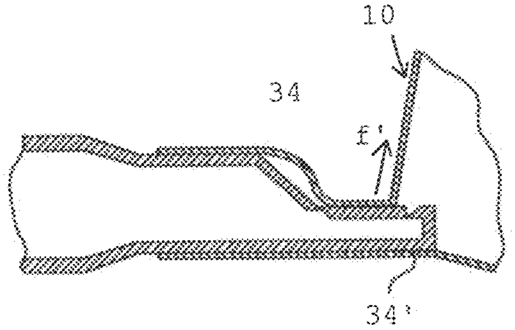

FIGS. 9(*a*) and (*b*) illustrates a modification of the embodiment shown in FIG. 8 and is modified in that, with respect to the point seal 34 of the top layer of the medical bag to the U-shaped profile portion 33 as the closure member, the opposed point seal 34' of the bottom layer of the medical bag 10 is displaced toward the inner cavity of the medical bag. In this case, the direction of the force as applied to the U-shaped profile portion 33 by the widening or expansion of the medical bag upon its opening process is illustrated by an arrow f' in FIG. 9(*b*) and forms an angle to the portion 33, which angle is increased, i.e., much more closer to the right angle. Thus, an increased value of the force as applied to the U-shaped profile portion 33 is obtained, resulting in a more reliable separating operation.

Figure 10A:
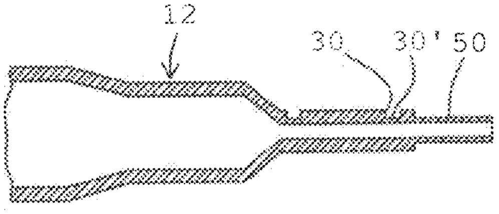
FIG. 10 is a cross-sectional view of the tip end part of the outlet port instill another embodiment, (*a*) showing a condition after completion of a molding process, (*b*) showing a sealed condition at a secondary process.
Figure 10B:
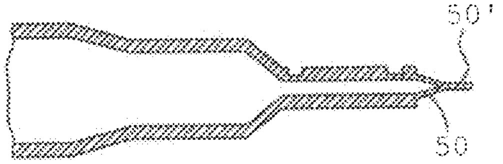

FIGS. 10(*a*) and (*b*) illustrate a modified embodiment, which is, however, similar to the previous embodiments in FIGS. 1, 8 and 9 in the provision of the U-shaped groove 30, which forms, at its bottom, the thin walled portion 30' as already explained. Namely, in the previous embodiments, the outlet port 12 as an injection-molded product has a closed structure at its end surface 12-6' (FIG. 2). For an injection molding of such a product of closed structure, a die set would be provided, which is constructed by an outer die having an inner recess corresponding to an outer profile of the outlet port 12 and a core or core pin having an outer shape corresponding to an inner profile of the outlet port and, then, a molten resin is introduced into a cavity between the outer die and the core for a molding process. During a molding of an outlet port 12 having a thin walled portion 30', a flow resistance of the molten resin is high at a recessed portion of the die for the formation of the thin walled portion 30' in the die set. Namely, due to the closed structure of the die set, an increased value of the injection pressure is essentially needed in order to obtain a desired flow rate of the resin at the recessed portion of the die. However, due to such an increased value of the injection pressure, a deflection of the core pin is likely generated, so that a formation of a thin walled portion 30' of a desired value of the thickness is apt to be difficult. Furthermore, such a deflection of the core pin makes a possibility to be likely that a service life of the die set is reduced. In order to combat this problem, in the embodiment in FIG. 10, the outlet port has, at its end, a thin walled tubular extended portion 50, which having an inner surface flashed with that of the reminded part, thereby obtaining a injection-molded product of an opened structure at its end surface. As a result of this opened structure, a stabled or reliable flow of the melt is obtained at the recessed portion of the die, which corresponding to the thin walled potion in the molded product, thereby obtaining a desired value of the wall thickness, on one hand and, on the other hand, a prolonged service life of the die set. In the condition of the product just separated from the die set, the thin walled tubular part 50 is kept opened. However, the succeeded second working is done, whereat the tubular part 50 is subjected to a pressing under a heat, so that a welded sealed part 50' is created as shown in FIG. 10(*b*), thereby obtaining a closed structure.

Figure 11:
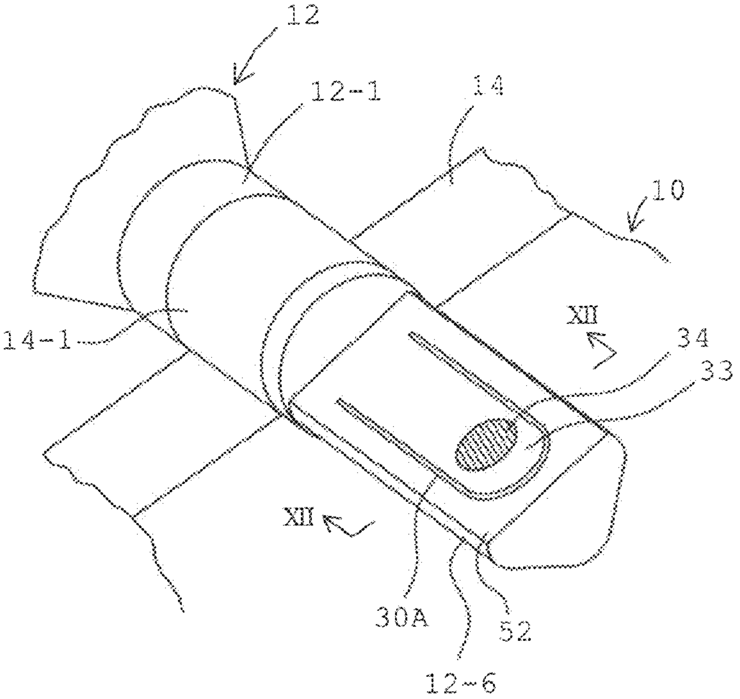
FIG. 11 is a perspective view of the tip end portion of the outlet port in a multi-cell container in another embodiment.
Figure 12:
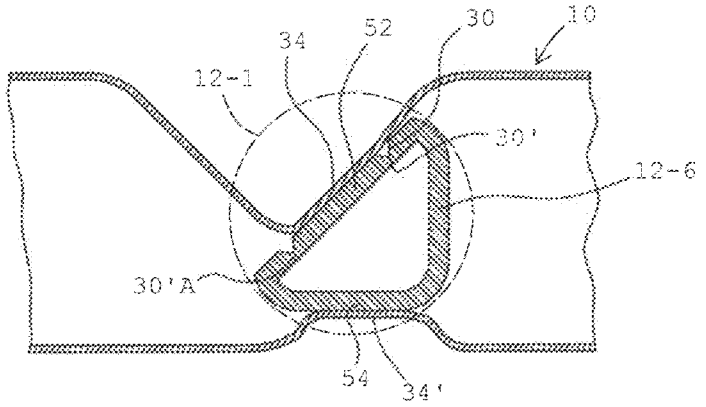
FIG. 12 is a cross-sectional view taken along lines XII-XII in FIG. 11.

FIGS. 11 and 12 illustrates a further another embodiment of the outlet port 12 having a closure member 33, which is inclined with respect to the plane of the medical bag 10. The outlet port 12 has a base portion 12-1 of a circular cross-sectional shape, from which a portion 12-6 of a triangle or delta shape integrally extends. The integrally extended portion 12-6 has a top surface 52 or a hypotenuse of the triangle shape of an inclination angle of a value about 45 degree with respect to the plane of the medical bag 10 or a horizontal plane. A closure member 33 on the top wall 52 is surrounded by a U-shaped groove 30 as a weak portion or thin walled portion and is securely welded to the top surface of a plastic film constructing the medical bag 10 by means of a point seal 34. Furthermore, the bottom plastic film layer constructing the medical bag 10 is welded to a horizontal bottom surface 54 of the integral extended portion 12-6 opposite to the inclined surface 52 by means of a point seal 34'.

In the embodiment, the expansion of the medical bag 10 as obtained when opening the bag, i.e., separating the weak seal causes to generate a fore in a vertical direction at the top and bottom welded parts 34 and 34' in the integral extended part 12-6 of the outlet port 12, which force is initially intensively applied at the areas where the spacing between the welded portions is narrow. As a result, the thin walled portion 30' at its bottom area 30'A in the U-shaped groove 30 is initially broken and the breakage is progressed in accordance with the increase in the degree of the expansion of the medical bag, thereby obtaining a positive breakage and opening of the closure member 33.

Figure 13:
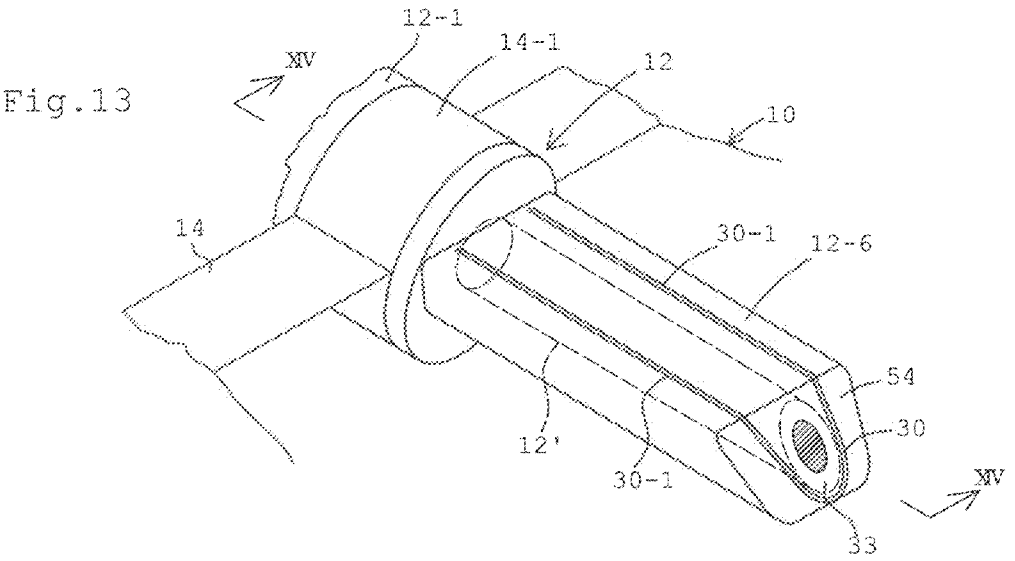
FIG. 13 is a perspective view of the tip end portion of the outlet port in a multi-cell container in further embodiment.
Figure 14A:
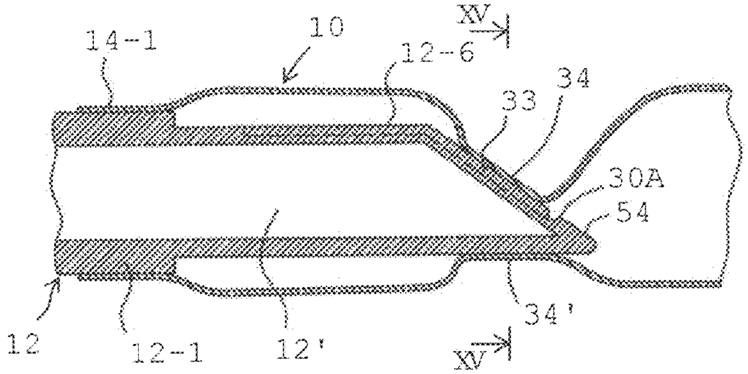
FIG. 14 is a cross-sectional view taken along lines XIV-XIV in FIG. 13, (*a*) showing an opened condition, (*b*) showing an opened condition.
Figure 14B:
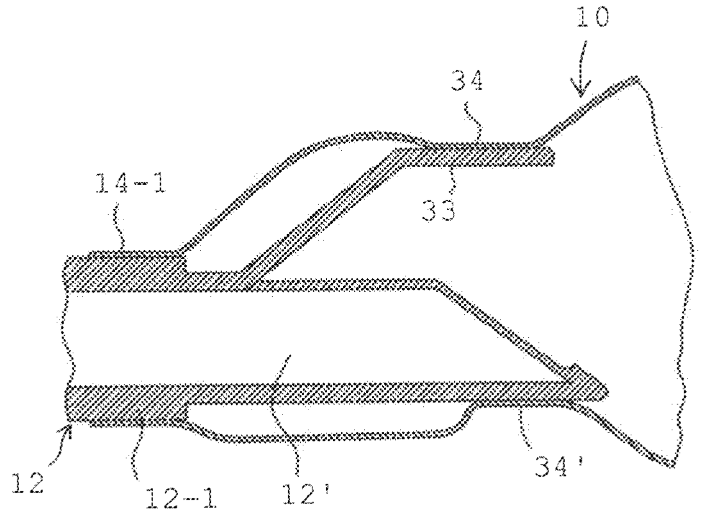
Figure 15:
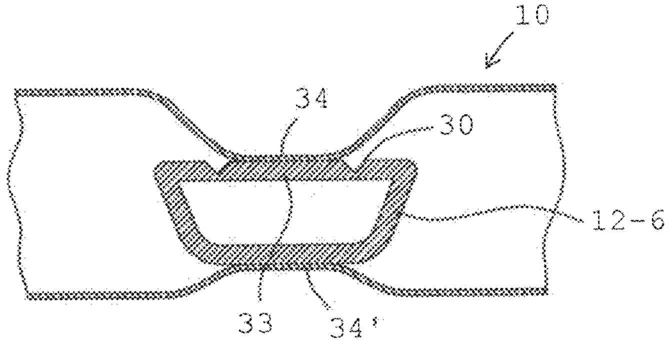
FIG. 15 is a cross-sectional view taken along lines XV-XV in FIG. 14.

FIGS. 13 to 15 illustrate still another embodiment of the outlet port, which has an integrally extended portion 12-6 having an inclined front end wall 54, on which end wall a closure member 33 surrounded by a U-shaped groove 30 as a thin walled portion is formed. The closure member 33 is welded to the opposed top layer of the medical bag at a welded portion 34. At the bottom layer, the medical bag is welded to the lower surface of the integrally extended part 12-6 of the outlet port 12 by means of the weld 34'. As shown in FIG. 13, the U-shaped groove 30 extends, at its opposed ends, to the upper edge of the inclined surface 54 and is, at the end of the integral extended portion 12-6, connected to respective straight grooves 30-1. The grooves extended to locations adjacent the connecting portion or loot portion of the integrally extended part 12-6 to the base portion 30-1 of the outlet port.

In this embodiment, the closure member 33 is provided on the inclined surface 54, so that an expansion of the medical bag upon its opening generates a force, which is applied to the U-shaped groove 30 as the breakable part also intensively at the narrower side of the lower part 30A of the groove as shown in FIG. 14(*a*), resulting in an initiation of a breakage of the part 30A, which is progressed by the successive expansion of the medical bag. This operation is advantageous in that a reliable opening of the closure member 33 is obtained. FIG. 14(*b*) illustrates a condition where the expansion of the medical bag 10 causes the closure member 33 to be separated and opened. Due to the arrangement that the straight grooves 30-1 connected to the U-shaped groove 30 extend to the location adjacent to the connecting point of the grooves to the root portion 12-1 of the outlet port, the inner passage 12' of the outlet port 12 is opened to the inside of the suspended medical bag 10 at a location adjacent the bottom of the bag, which is under a suspended condition for practicing an infusion, which makes it possible that a discharge of the medical liquids from the bag is completed with nil or minimized residue.

Figure 16:
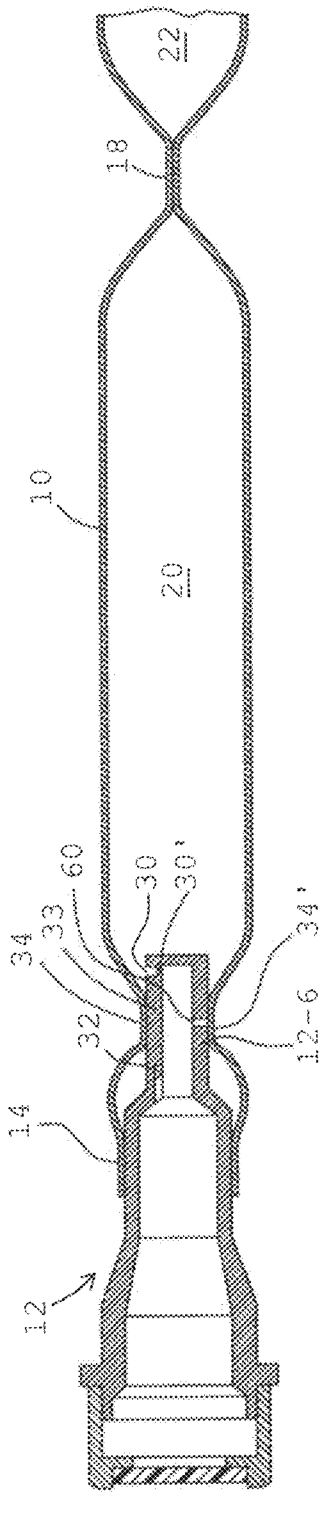
FIG. 16 is a partial cross-sectional view of the further embodiment of the multi-cell container according to the present invention.
Figure 17:
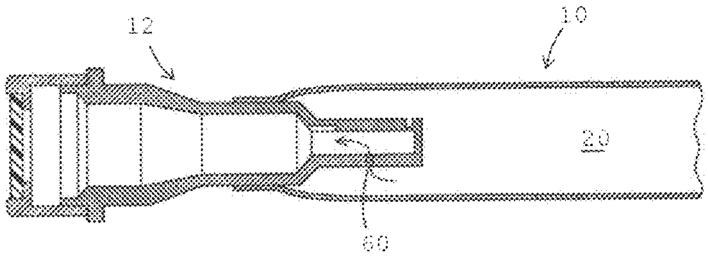
FIG. 17 is a partial cross sectional view of the multi-cell container shown in FIG. 16 when practicing a sterilizing process.
Figure 18:
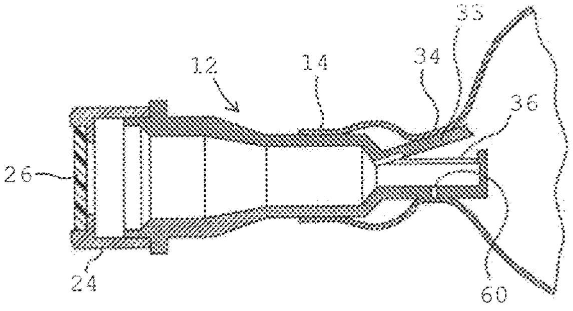
FIG. 18 is partial view of a connecting portion of the outlet port to the medical bag of the multi-chamber container in the embodiment shown in FIG. 16, when the medical bag is in its opened condition.

FIGS. 16 to 18 illustrate a still further embodiment of the present invention, which is modified from the embodiment in the first embodiment shown in FIGS. 1 to 6 in that a sterilization of the outlet port when the container is produced is done under a wet heat condition by a vapor of the medical liquid as obtained by heating the medical liquid stored in the medical bag. As well known, such sterilization at a wet heat condition is advantageous in the efficiency over sterilization at a dry heat condition. A structural difference of the instant embodiment over the first embodiment in FIG. 1 is in a provision of a communication hole or aperture 60 as a second opening of the present invention, which hole is formed in the rectangular cross sectional portion 12-6 of the outlet port 12 at a location faced with the U-shaped profile portion 33 as a closure member and is sealed by a weld 34' when the product is shipped as shown in FIG. 16. Namely, the welded portion 34' is constructed by pressing the cut of synthetic film cut to the rectangular cross-sectional portion 12-6 at a non-separable temperature. Furthermore, the communication hole 60 is of a size, which is small enough to substantially prevent a free passage of the liquid flow and large enough allowing a communication of the vapor of the medical liquid and which is, for example, in a range between 0.1 mm to 3 mm.

A sterilization process of the double cell container shown in FIG. 16 will now be explained. The double cell container prior to subjecting to the sterilization process is shown in FIG. 17, wherein a welding of the opposed surfaces of the medical bag to the U-shaped profile portion 33 and the rectangular cross-sectional portion 12-6, respectively is not yet completed, i.e., the formation of welds 34 and 34' is not yet completed. However, a connection of the outlet port 12 to the peripheral strong seal and an introduction of the medical liquids into the compartments 20 and 22 are completed. The U-shaped profile portion 33 is integrally formed with the outlet port. Contrary to this, the communication hole 60 is opened, i.e., the compartment 20 is in communication with the outlet port 12 via the communication hole 60. However, the small flow area of the communication hole 60 prevents substantially a liquid flow to the outlet port 12 from being occurred. During a sterilization process, the medical bag is heated at a desired temperature, so that a vapor of a medical liquid is generated in the compartment 20 adjacent the outlet port 12. The vapor of the medial liquid is introduced into the outlet port 12 via the communication hole 60 as shown by an arrow in FIG. 7 and is effective for sterilizing the outlet port 12. After the completion of the sterilization process, the rectangular cross-sectional portion 12-6 of the outlet port 12 is pressed between the top and bottom cuts of synthetic film constructing the medical bag 10 by a welding device, so that the welds 34 and 34' as shown in FIG. 16 are obtained.

FIG. 18 illustrates an expanded condition of the medical bag 10 at a connecting portion to the outlet port 12 when the bag is opened for mixing medical liquids between the compartments as is basically identical to FIG. 6. Namely, due to the welded structure of the medical bag 10 at the welds 34 and 34', the expansion of the medical bag upon its opening causes the U-shaped profile portion 33 as the closure member to open. The resultant formation of the opening or aperture 36 allows the mixed liquids to be introduced into the outlet port 12

Figure 19:
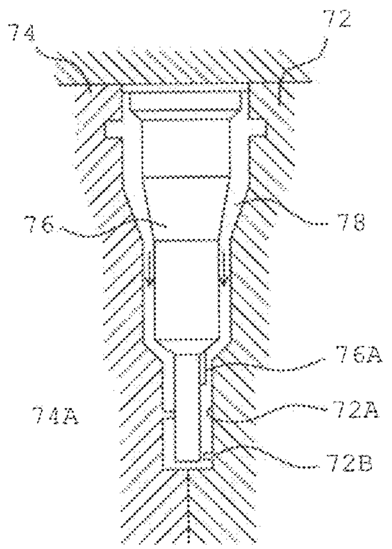
FIG. 19 is a cross-sectional view of a die arrangement used for a molding of the outlet port of the multi-chamber container in the embodiment shown in FIG. 16.

FIG. 19 illustrates a molding process of the outlet port 12 in FIG. 16 from a synthetic resin material. A die set is provided, which is constructed by a pair of split dies or outer dies 72 and 74 and a core or core pin 76, between which dies and core a cavity 78 having a shape corresponding to a profile of the outlet port 12 in FIG. 16 is formed. A reference numeral 72A illustrates a recessed portion of the split die 72 for forming the U-shaped profile portion 33 of the outlet port. A reference numeral 76A illustrates a projected portion of the core 76 for forming the integral hinge part 32 of the outlet port 12. Furthermore, a reference numeral 74A illustrates a portion of the split die 74 for forming the communication hole 60 of the outlet port 12, which portion 74A is located to oppose the recessed portion 72A of the split die 72 for forming the U-shaped profile portion 33. In order to practice a molding of an outlet port 12, a molten synthetic resin is introduced into the die cavity between the split dies 72 and 74 and the core 76 as shown by arrows in FIG. 19. Due to the restricted flow passage at the projected portion 76A of the core 76 and the projected portion 72B of the split die 72, a flow resistance is generated, so that the core 76 extending in cantilever fashion downwardly is urged laterally toward the split die 74. However, the core 76 maintains its desired centered position regardless of the lateral urging force, due to the fact that the free end of the core 76 is rested on or supported by the projected portion 74A of the split die 74. As a result, a desired value of the thickness of the thin walled portion 30' (FIG. 16) at the bottom of the groove 30 of the outlet port 12 as a molded product is obtained. Thus, an excessively increased value of the wall thickness is prevented, which otherwise may cause a breakage of the thin walled portion and the resulting separating operation of the U-shaped profile portion 33 as the closure member not to properly occur. Contrary to this, according to the present invention, a desired position of the core 76 during a molding operation is maintained, resulting in a desired control of the wall thickness.

The invention claimed is:

1. A multi-chamber container comprising:

a medical bag comprising a flexible film and configured to store medicines; and an outlet port mounted to the medical bag and configured to discharge the medicines, wherein the medical bag has a partition wall dividing the inside of the medical bag into a plurality of compartments configured to store the medicines, respectively, said partition wall has a welded portion comprising opposed inner surfaces of the medical bag welded together such that the welded portion separates by a pressing force applied to the medical bag and the medicines stored in the compartments are mixed with each other, said outlet port has an extended portion extending inwardly to the inside of the medical bag and a closure member formed integral with the outlet port in said extended portion of the outlet port and having a U-shaped profile, said closure member has a sealed point connected to a surface of the medical bag in the inside of the medical bag such that said closure member is opened by expansion of a portion of the medical bag when the partition wall is separated and causes the outlet port to communicate with the inside of the medical bag, the extended portion has a recess portion, an integrated hinge portion, and a thin wall portion connecting to the closure member such that the closure member is an integral portion of the outlet port, said thin wall portion of the extended portion is configured to be broken by the expansion of the portion of the medical bag such that the closure member is pulled by the sealed point, rotated about the integrated hinge portion and is opened by breaking the thin walled portion formed along the periphery of the closure member, and the sealed point of the closure member is positioned away from the recess portion and toward the partition wall.

2. A multi-chamber container comprising:

a medical bag comprising a flexible film and configured to store medicines; and an outlet port mounted to the medical bag and configured to discharge the medicines, wherein the medical bag has a partition wall dividing the inside of the medical bag into a plurality of compartments configured to store the medicines, respectively, said partition wall has a welded portion comprising opposed inner surfaces of the medical bag welded together such that the welded portion separates by a pressing force applied to the medical bag and the medicines stored in the compartments are mixed with each other, said outlet port has an extended portion extending inwardly to the inside of the medical bag and a closure member formed integral with the outlet port in said extended portion of the outlet port and having a U-shaped profile, said closure member has a sealed point connected to a surface of the medical bag such that the closure member is opened by expansion of a portion of the medical bag when the partition wall is separated and causes to form an opening for communicating the outlet port with the inside of the medical bag, the closure member is positioned on one side of the extended portion of the outlet port and configured to form the opening at the one side of the outlet port, the extended portion has a recess portion, an integrated hinge portion, and a thin wall portion connecting to the closure member such that the closure member is an integral portion of the outlet port, said thin wall portion of the extended portion is configured to be broken by the expansion of the portion of the medical bag such that the closure member is pulled by the sealed point, rotated about the integrated hinge portion and is opened by breaking the thin walled portion formed along the periphery of the closure member, and the sealed point of the closure member is positioned away from the recess portion and toward the partition wall.

3. A multi-chamber container comprising:

a medical bag comprising a flexible film and configured to store medicines; and an outlet port mounted to the medical bag and configured to discharge the medicines, wherein the medical bag has a partition wall dividing the inside of the medical bag into a plurality of compartments configured to store the medicines, respectively, said partition wall has a welded portion comprising opposed inner surfaces of the medical bag welded together such that the welded portion separates by a pressing force applied to the medical bag and the medicines stored in the compartments are mixed with each other, said outlet port has an extended portion extending inwardly to the inside of the medical bag and a closure member formed integral with the outlet port in said extended portion of the outlet port and having a U-shaped profile, said closure member has a sealed point connected to a surface of the medical bag in the inside of the medical bag such that the closure member is opened by expansion of a portion of the medical bag when the partition wall is separated and causes to form an opening for communicating the outlet port with the inside of the medical bag, the closure member is mounted on a portion of the extended portion which has the axis extending in a offset relationship with respect to the axis of the outlet port, the extended portion has a recess portion, an integrated hinge portion, and a thin wall portion connecting to the closure member such that the closure member is an integral portion of the outlet port, said thin wall portion of the extended portion is configured to be broken by the expansion of the portion of the medical bag such that the closure member is pulled by the sealed point, rotated about the integrated hinge portion and is opened by breaking the thin walled portion formed along the periphery of the closure member, and the sealed point of the closure member is positioned away from the recess portion and toward the partition wall.

4. A multi-chamber container according to claim 3, wherein the closure member is formed on a portion of the extended portion having an increased offset amount.

5. A multi-chamber container according to claim 4, wherein the partition wall of the medical bag is formed at an opposite side of the closure member in the medical bag.

6. A multi-chamber container according to claim 1, wherein said closure member is configured to be rotated with respect to the medical bag.

7. A multi-chamber container according to claim 1, wherein the thin wall portion of the extended portion is configured to be broken by the expansion of the portion of the medical bag such that the closure member is entirely separated from the outlet port.

8. A multi-chamber container according to claim 1, wherein the outlet port is a molded product comprising a resin material and having an opened structure at an end portion.

9. A multi-chamber container according to claim 1, wherein the outlet port has an inclined surface on which the closure member is provided.

10. A multi-chamber container according to claim 7, wherein said thin wall portion is extended to a portion of the extended portion adjacent a root portion where the outlet port is connected to the surface of the medical bag.

11. A multi-chamber container according to any one of claims 1 to 6 and 7 to 10, wherein said outlet port has a second opening being closed by a surface of the medical bag and configured to form a communication for executing a sterilizing operation.

12. A multi-chamber container comprising:

a medical bag comprising a flexible film and configured to store medicines; and an outlet port mounted to the medical bag and configured to discharge the medicines, wherein the medical bag has a partition wall dividing the inside of the medical bag into a plurality of compartments configured to store the medicines, respectively, said partition wall has a welded portion comprising opposed inner surfaces of the medical bag welded together such that the welded portion separates by a pressing force applied to the medial bag and the medicines stored in the compartments are mixed with each other, the outlet port has a closure member formed integral with the outlet port in an extended portion of the outlet port positioned inside the medical bag and having a U-shaped profile, said closure member has a sealed point connected to a surface of the medical bag and is configured to be opened by expansion of a portion of the medical bag when the partition wall is separated and causes to form a first opening for communicating the outlet port with the inside of the medical bag, said outlet port has a second opening being closed by the surface of the medical bag and configured to be connected to the outlet port to the inside of the medical bag, the extended portion has a recess portion, an integrated hinge portion, and a thin wall portion connecting to the closure member such that the closure member is an integral portion of the outlet port, said thin wall portion of the extended portion is configured to be broken by the expansion of the portion of the medical bag such that the closure member is pulled by the sealed point, rotated about the integrated hinge portion and is opened by breaking the thin walled portion formed along the periphery of the closure member, and the sealed point of the closure member is positioned away from the recess portion and toward the partition wall.

13. A multi-chamber container according to claim 2, wherein the outlet port is a molded product comprising a resin material and having an opened structure at an end portion.

14. A multi-chamber container according to claim 3, wherein the outlet port is a molded product comprising a resin material and having an opened structure at an end portion.

15. A multi-chamber container according to claim 12, wherein the outlet port is a molded product comprising a resin material and having an opened structure at an end portion.

* * * * *